United States Patent [19]

Jackson et al.

[11] Patent Number: 5,319,966
[45] Date of Patent: Jun. 14, 1994

[54] DETERMINING LOCATION AND COMPOSITION OF LIQUID CONTAMINANTS IN GEOLOGIC FORMATIONS

[75] Inventors: Richard E. Jackson, Austin; John F. Pickens, Round Rock, both of Tex.

[73] Assignee: Intera, Inc., Austin, Tex.

[21] Appl. No.: 892,787

[22] Filed: Jun. 3, 1992

[51] Int. Cl.$^5$ .................... E21B 49/08; E21B 43/27; G01N 33/24
[52] U.S. Cl. .................... 73/153; 73/155; 436/27; 436/30; 166/250; 166/270
[58] Field of Search .................... 73/151, 155, 153; 436/25, 27, 28, 30; 166/250, 269, 270

[56] References Cited

U.S. PATENT DOCUMENTS

| | | | |
|---|---|---|---|
| 2,318,689 | 5/1943 | Hodell et al. | 436/28 X |
| 2,387,513 | 10/1945 | Hocott | 436/25 X |
| 4,158,957 | 6/1979 | Deans et al. | 166/250 X |
| 4,168,746 | 9/1979 | Sheely | 436/27 X |
| 4,223,725 | 9/1980 | Teasdale et al. | 166/250 |
| 4,261,812 | 4/1981 | Newcombe | 208/188 |
| 4,444,654 | 4/1984 | Cargle et al. | 208/188 |
| 4,681,165 | 7/1987 | Bannister | 166/312 |
| 4,706,749 | 11/1987 | Hayes et al. | 166/267 |
| 4,742,459 | 5/1988 | Lasseter | 73/151 X |
| 4,997,313 | 3/1991 | Gibson et al. | 405/128 |

OTHER PUBLICATIONS

Mackay and Cherr, "Groundwater contamination: Pump-and-treat remediation," *Environ. Sci. Technol.*, vol. 23, No. 6 (1989).
Fountain and Hodge, "Extraction of Organic Pollutants Using Enhanced Surfactant Flushing-Initial Field Test (Part I)", N.Y. State Center for Hazardous Waste Mgmt (1992).
Mackay, "Characterization of the Distribution and Behavior of Contaminants in the Subsurface," *Ground Water and Soil Contamination Remediation: Toward Compatible Science, Policy and Public Perception*, National Academy Press (1990).
"Groundwater Contamination," *Complex Cleanup-The Environmental Legacy of Nuclear Weapons Production*, Congress of the U.S., Office of Technology Assessment, Feb. 1990.
Stipp, "Throwing Good Money at Bad Water Yields Scant Improvement," *Wall St. J.*, May 5, 1991 at 1.
Pickens and Jackson, "Measurement of Distribution Coefficients Using a Radial Injection Dual-Tracer Test," *Water Resources Research*, vol. 17, No. 3 (1981).
"Groundwater Treatment-EPA cites failures of most common method," *Superfund Report*, p. 2 (Nov. 8, 1989).
"EPRA Acknowledges Groundwater Cleanup Impossible at Some Superfund Sites," *Inside E.P.A.* (Sep. 20, 1991).

*Primary Examiner*—Robert J. Warden
*Assistant Examiner*—E. Leigh Dawson
*Attorney, Agent, or Firm*—Pravel, Hewitt, Kimball & Krieger

[57] ABSTRACT

A method is provided for locating non-aqueous phase liquid in an aquifer. An aqueous solution having the capacity to solubilize the contaminating liquid to concentrations greater than the solubility of the contaminant in water is injected and produced through a well. Chemical concentrations in produced fluid samples are interpreted to locate the contaminating liquid. Produced fluid samples are chemically analyzed to determine composition of the contaminant.

16 Claims, 5 Drawing Sheets

DETERMINING LOCATION AND COMPOSITION OF LIQUID CONTAMINANTS IN GEOLOGIC FORMATIONS

BACKGROUND OF THE INVENTION

1. Field of the Invention

This invention relates to the removal of contaminating materials from the earth. More particularly, the invention relates to locating and determining the composition of non-aqueous phase liquids (NAPLs) which may contaminate groundwater. The information gained from this invention is used in planning and executing remediation processes.

2. Description of Related Art

Contamination of groundwater has been found to be widespread and often very expensive to remedy. Health-threatening organic chemicals detected in groundwater have caused the greatest difficulties in remediation of contamination. Since the passage of environmental legislation in the United States in the 1980's, the expenditure of more than a billion dollars for site investigations and cleanup activities has advanced considerably the knowledge of the nature of organic contamination of groundwater (D. M. McKay and J. A. Cherry, *Environ. Sci. Technol.*, Vol. 23, No. 6, 1989). Hundreds of plumes of organic contaminants have been delineated in the U.S. by networks of monitoring wells which are used to sample groundwater surrounding the wells for dissolved contaminants.

Because of the complexity of geologic formations and the fact that groundwater normally is not stationary but moves through soil or rock layers, it has been extremely difficult to determine the location of the free liquid contaminants which supply the dissolved materials contaminating groundwater. The dissolved organic contaminants in groundwater may have their origin in a spill or leak of organic liquid which occurred miles from the location of the contaminated water.

If organic liquids are lighter than water, they move downward through the vadose or partially air-saturated zone near the surface of the earth and accumulate on top of the water table. Such light non-aqueous phase liquids are referred to as "LNAPLs." The most commonly occurring contaminating LNAPL is motor fuel, such as gasoline. Motor fuels may contain small amounts of toxic chemicals such as benzene.

Some organic liquids lost near the surface of the earth have a higher density than water and continue to settle vertically through the water-saturated zone below the water table. Such liquids are called DNAPLs (dense non-aqueous phase liquids). Examples of DNAPLs are chlorinated hydrocarbons such as perchloroethylene and polychlorinated biphenyls, or PCBs. DNAPLs are particularly difficult to locate in the earth because they can continue to settle through the saturated zone until a low-permeability layer of soil or rock is reached, at which point they accumulate on top of the layer. If the low-permeability layer is of limited extent, the DNAPL may spill over from a higher to a lower low-permeability elevation. Thus, because of complex geology the route of DNAPLs moving downward through the earth is often not vertical. Also, there may be very limited information concerning the source of the contaminant.

The common method of remediation of groundwater contamination is simply to pump the contaminated water from the earth, to strip the contaminating chemicals from the water and to reinject or otherwise dispose of the water. Experience has taught that an initial decrease in contaminant concentrations in the water is followed by a leveling of concentration of contaminants. It is believed that the leveling of concentration of contaminants occurs because the water is continuing to be contaminated by dissolving free liquids present somewhere in the aquifer. Not knowing the size and location of NAPL pools and zones of residual NAPL makes it impossible to predict how long a pump-and-treat program must operate in order to clean the aquifer (McKay and Cherry, supra, 1989).

The solubility in water of some NAPLs which commonly occur in groundwater is as follows:

| | |
|---|---|
| Benzene: | 1780 mg/L |
| Carbon tetrachloride: | 785 |
| Trichloroethylene | 1100 |

It is known that the solubility of organic materials in an aqueous solution can be increased far above these values by adding certain surfactants to water. Above a certain surfactant concentration, called the "critical micelle concentration," the surfactant solution contains micelles of surfactant molecules, which are aggregates of the surfactant molecules. The interior of the micelles, being hydrocarbon-like, can dissolve organic material or NAPLs to a much higher concentration than that due to the solubility of the NAPL in water. Increased solubility in solutions that are completely miscible with water can also be achieved by addition of cosolvents such as alcohols or ketones to water. Such solvent effects can also be used to increase the solubility of NAPLs to a concentration above the solubility in groundwater.

The extraction of organic pollutants using surfactant solutions has been tested (J. C. Fountain and D. S. Hodge, "Extraction of Organic Pollutants Using Enhanced Surfactant Flushing—Initial Field Test (Part 1)," New York State Center for Hazardous Waste Management, State University of New York at Buffalo, 1992). In the test, a surfactant solution was injected in some wells and produced from other wells. The concentration of a chlorinated hydrocarbon in the effluent surfactant solution was increased to more than 20 times its aqueous solubility. A 50-fold increase was observed in point samples taken during the test. Even higher increases could be achieved at higher surfactant concentrations. Other surfactants may solubilize certain NAPLs more effectively.

U.S. Pat. No. 4,997,313 discloses a method for use of an aqueous surfactant solution to remove organic contaminants from subsurface soil layers. The process is carried out continuously with the application of the surfactant solution to the surface of the earth and the removal of the solution containing the contaminant from a recovery well within the treatment area.

Although solubilizing solutions can be used to assist in removing contaminating NAPLs from soil or rock layers where the NAPLs may continue to dissolve in and contaminate large amounts of groundwater, there remains the problem of locating the undissolved NAPLs in the earth. It is known to drill wells into an aquifer and remove samples of the solids and liquids contained in the pores of the solids and analyze the liquids to determine the amount and composition of NAPLs. It is also known to produce fluids from the wells and to analyze the fluids for contaminating NAPLs, but if the NAPL is not present at high enough saturations in the pore space immediately around the well, only dissolved NAPL can be produced and the presence of liquid or undissolved NAPL will not be detected around the well. The NAPL can be present where the liquid fills only a fraction of the pore spaces of a geologic formation, up to about 20-35 per cent, depending on the size and structure of pores, and it will not flow through the formation because it is trapped in the pores by capillary forces. Ganglia of NAPL then are surrounded by water. But, at these saturations in the pore spaces there is sufficient NAPL to dissolve in and contaminate very large volumes of groundwater flowing through the formation. At liquid saturations above about 20-35 percent of the pore space, the NAPL will flow through the pore spaces and can be produced into a well to prove the presence of liquid around the well.

Many wells drilled in the search for free liquid NAPLs in the earth show no indication of free liquid—only dissolved NAPL. There is a long-felt need for a method of sampling a much larger volume of formation around these wells not having free liquid present at the well, to determine if free liquid is present in the vicinity of the well. Not only is there a need to determine if a NAPL is nearby a well, but there is a need to determine the likely composition of that liquid if it is present. Should the NAPL be composed of more than one component, knowledge of the identity and approximate mass fraction of each component is needed, so the environmental remediation engineer can design an effective treatment system. The location of NAPL and information on its composition can make practical the remediation of groundwater contamination which would otherwise exist as a long-term threat to health and a clean environment.

SUMMARY OF THE INVENTION

A method is provided for predicting the location of non-aqueous phase liquids (NAPLs) in a subsurface formation by injecting through a well into the formation a selected volume of water-miscible solution which is capable of solubilizing the contaminating NAPLs. The solubilizing solution is then produced through a well, which may be the same well through which it is injected, and the produced solution is chemically analyzed. A greater concentration of contaminating material in the produced solution than is present in the groundwater previously produced from the well indicates the presence of a contaminating NAPL in the vicinity of the well. From the prediction of the location of the segment of the formation contacted by the solubilizing solution, the location of non-aqueous phase liquids in the formation is predicted. Chemical analysis of the produced solution determines the composition of the contaminating liquid in the formation.

DESCRIPTION OF PREFERRED EMBODIMENTS

Figure 1:
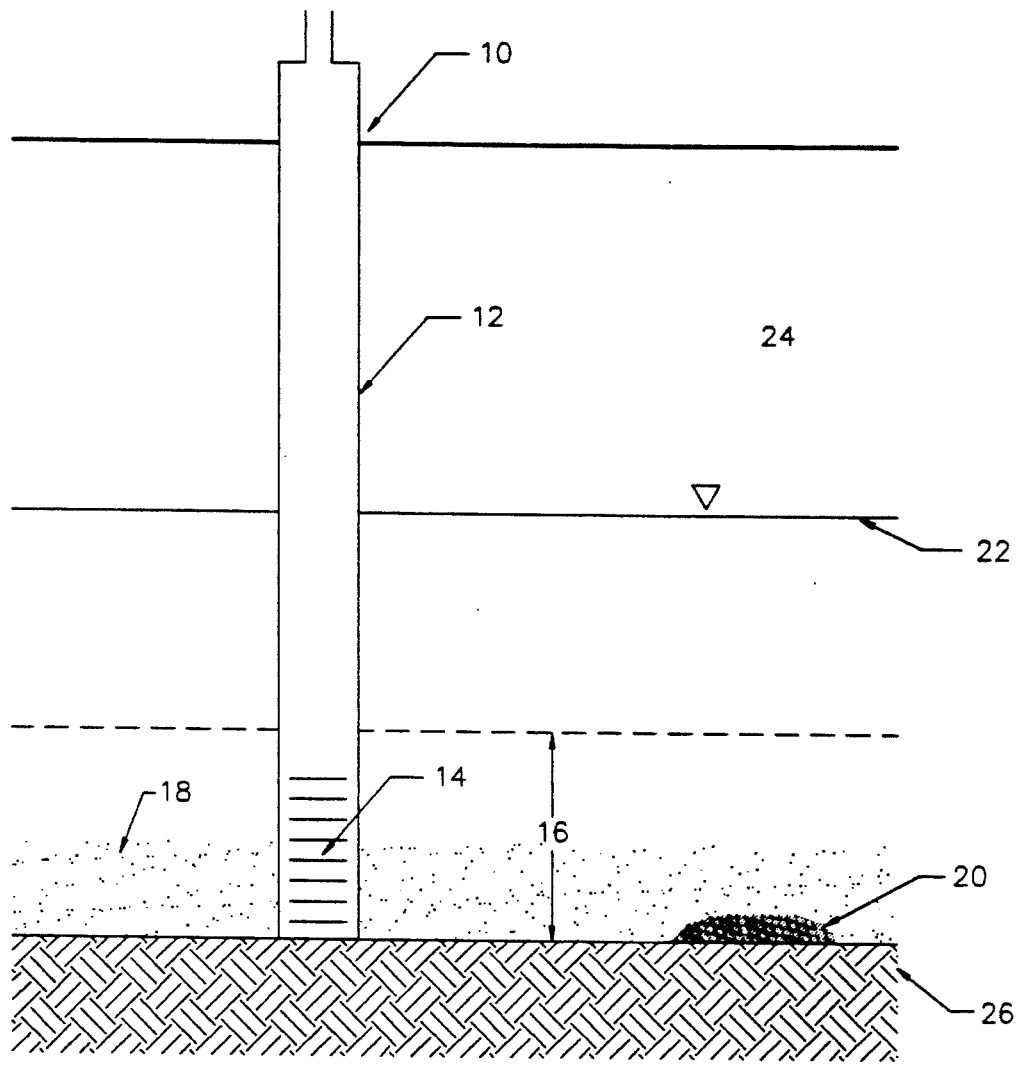
FIG. 1 is a cross-section view of a well in a formation containing NAPLs dispersed near the well and dispersed NAPL along with pools of DNAPL at a distance from the well.

Referring now to FIG. 1, well 10 is drilled into the earth and casing 12 is placed in the well. Screen 14 is at the lower end of casing 12 to allow fluids to enter or leave the well. Casing 12 is sealed in the well using conventional techniques. Screen 14 is placed within permeable zone 16 in the earth. The screen may be placed over only a selected segment where there is particular interest in determining the presence of NAPL. Other techniques, such as perforated casing and inflatable packers may be used to isolate flow to a selected segment of the wellbore.

The lower portion of permeable zone 16 contains dispersed droplets or ganglia 18 of DNAPL. Zone 16 is below the water table 22 in the well. Zone 16 is thus within what is termed the "saturated zone" in the earth. The vadose zone 24 in the earth exists above the water table 22. In addition to dispersed contaminant 18, a "pool" of DNAPL 20 exists directly above low permeability layer 26. This pool is a region of the geologic formation which contains DNAPL at a saturation high enough for the liquid to flow through the rock.

Groundwater produced into well 10 through screen 14 will contain dissolved contaminant from the NAPL. The concentration of contaminant may be well below the solubility limit in groundwater, because dispersed contaminant 18 is not present throughout zone 16. However, the groundwater in well 10 will be contaminated, and the location and composition of undissolved liquid contaminant are to be identified by the method of this invention.

In the method of this invention, a solubilizing solution is injected into well 10 through screen 14. A volume of solution is selected to penetrate the permeable zone 16 to a selected distance. Alternatively, a selected volume or slug of solubilizing solution is injected and driven farther into the zone 16 by injection of water behind the solubilizing solution. For design and analysis purposes, the average radial front position $\bar{r}$ of the injected solubilizing solution can be estimated using the expression:

$$r = \left[ \frac{Q \Delta t_{inj}}{\pi b \theta} \right]^{\frac{1}{2}}$$

where
$\bar{r}$ is the average radial front position;
Q is the injection rate;
b is the effective thickness of the permeable zone 16;
$\theta$ is the porosity in the effective thickness of permeable zone 16;
$\Delta t_{inj}$ is the time of fluid injection (either solubilizing solution or water driving the solution).

Since the injected solubilizing solution will experience dispersion in the radial direction around the well, analysis of the concentration history of chemicals produced can be used to estimate the dispersivity of the injected solution in the formation, using techniques described in the paper "Measurement of Distribution Coefficients Using a Radial Injection Dual-Tracer Test." *Water Resources Research*, Vol. 17, No. 3, pp. 529-44 (1981), which is incorporated herein by reference for all purposes. The dispersivity can then be used in calculating concentration of solubilizing solution in the permeable zone 16 during the injection and withdrawal phases. Preferably, an inert tracer is added to the solubilizing solution at a known concentration before the solution is injected, and the measured concentrations of this tracer is used in analyzing results to determine produced concentrations of solubilizing solution.

Measurements in the laboratory can be used to measure any decrease in velocity of the selected surfactant solution relative to that of groundwater. This retardation factor for the surfactant solution in solids from the geologic formation is measured using the method described in the paper "Laboratory Column Measurement of VOC Retardation Factors and Comparison with Field Values," *Ground Water*, Vol. 29, No. 2, pp. 260-266 (1991), which is incorporated herein by reference for all purposes. This retardation factor can be used together with the numerical techniques described in the paper "Measurement of Distribution Coefficients Using a Radial Injection Dual-Tracer Test," supra.

To predict the distance which the solubilizing solution has penetrated the zone 16 from the well after a selected volume has been injected, in addition to the calculations based on volume injected as described above, means for in situ measurement of the location of the injected solution may be employed. Such means include geophysical measurements at the surface or between wells of, for example, changes in electrical resistivity as solubilizing solution having a resistivity different from the groundwater resistivity is injected, using techniques known in industry.

Logs can be obtained in individual wells to determine the presence of NAPL immediately adjacent the wellbore. For example, neutron logs can be used to detect halogenated hydrocarbons at a saturation below the point the NAPL will flow into a well. The presence of NAPL adjacent the wellbore will not allow the method of this invention to investigate the presence of the same liquid at a location remote from the well, but the presence of NAPL can be confirmed by this invention and the composition of the NAPL can be determined.

Figure 2:
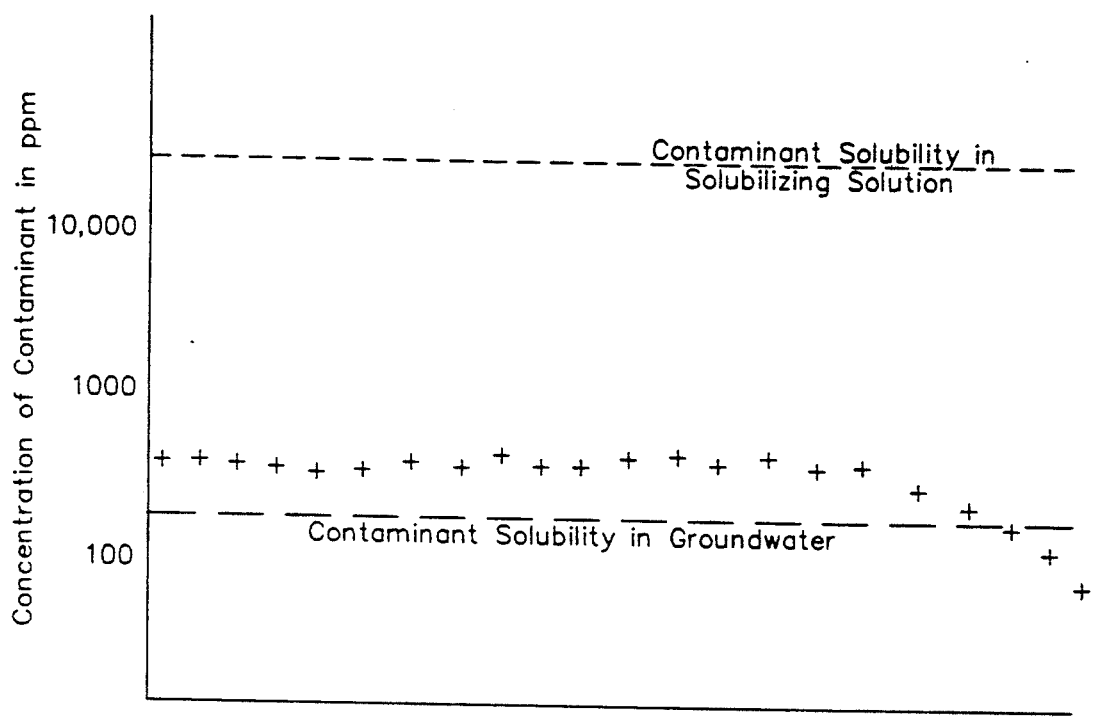
FIG. 2 is an illustration of the variation of contaminant concentration from solubilizing solution produced from a well under conditions sketched in FIG. 1.

FIG. 2 is a plot illustrating the concentration of contaminant expected to be produced from well 10 after the solubilizing solution has been injected. Because the solubilizing solution has significantly greater capacity for dissolving the contaminant, the concentration of contaminant in the aqueous volume produced back from well 10 is significantly greater than the solubility in groundwater. Dispersed contaminant near well 10 is dissolved by the solubilizing solution and produced immediately upon the beginning of production from the well, since the solubilizing solution has not yet removed all contaminant from near the well. Some of the produced water comes from above the zone of dispersed contaminant droplets 18 and does not contain contaminant. The mixture produced contains contaminant above the solubility in groundwater until the concentration of solubilizing materials in the injected solution decreases to a low value. When the injected solubilizing solution has been produced, the concentration of contaminant in produced water approaches the concentration in groundwater produced before injection of the solubilizing solution.

Figure 3:
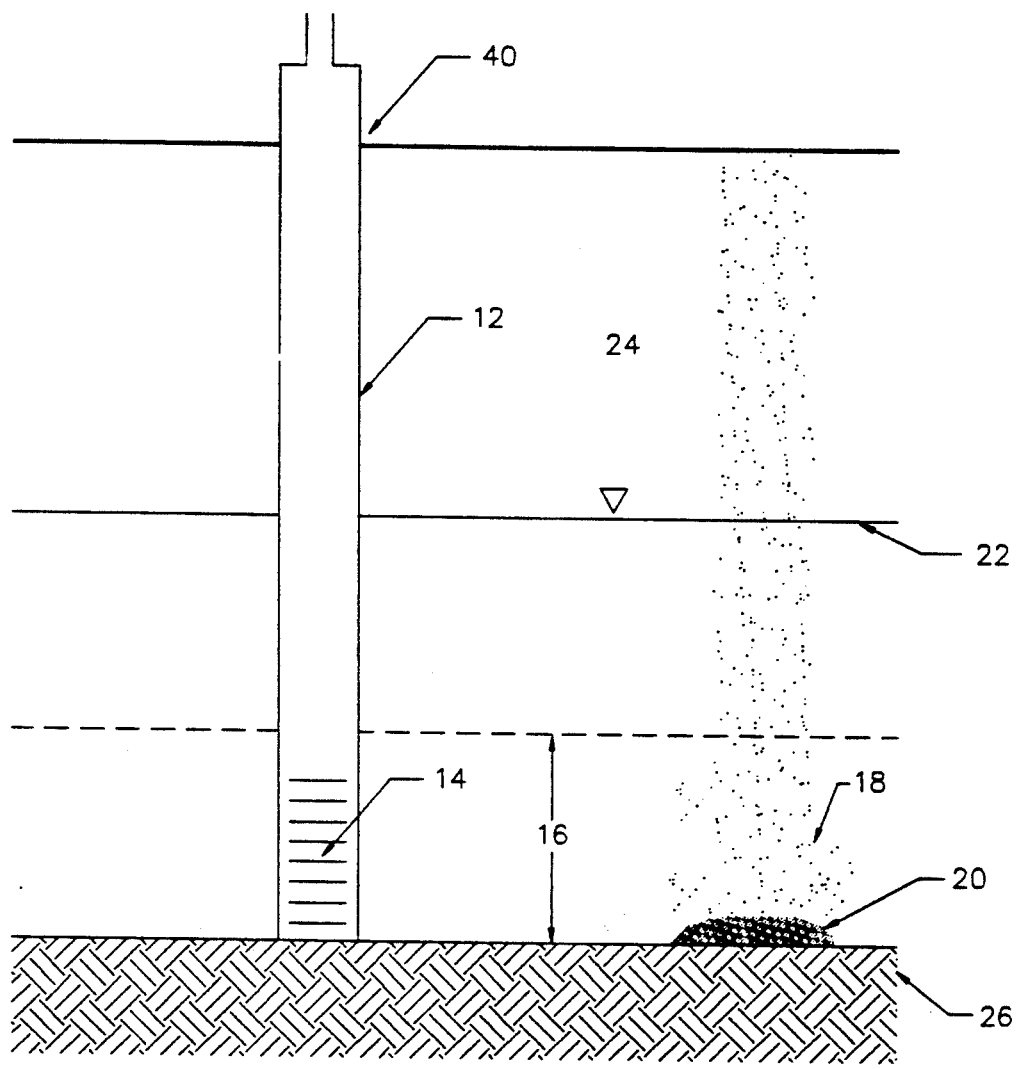
FIG. 3 is a cross-section view of a well in a formation containing dispersed NAPLs and pools of free liquid DNAPL at a distance away from the well.

Referring to FIG. 3, well 40 is drilled into the earth and casing 12 is placed in the well. Well 40 is drilled in an area of the aquifer where neither dispersed or pooled contaminant is present, but ganglia or dispersed contaminant 18 is present along with pooled contaminant 20 at a distance remote from well 40. Well 40 may be equipped to inject and produce fluids into the same zone 16 as is present in well 10. Water table 22 is also present above the screened interval 14 of well 40, although it may be at a different depth than around well 10.

A selected volume of solubilizing solution is injected into well 40 such that the radius of the injected solubilizing solution extends beyond dispersed contaminant 18 and pool of contaminant 20. The aqueous solubilizing solution is then produced back through well 40.

Figure 4:
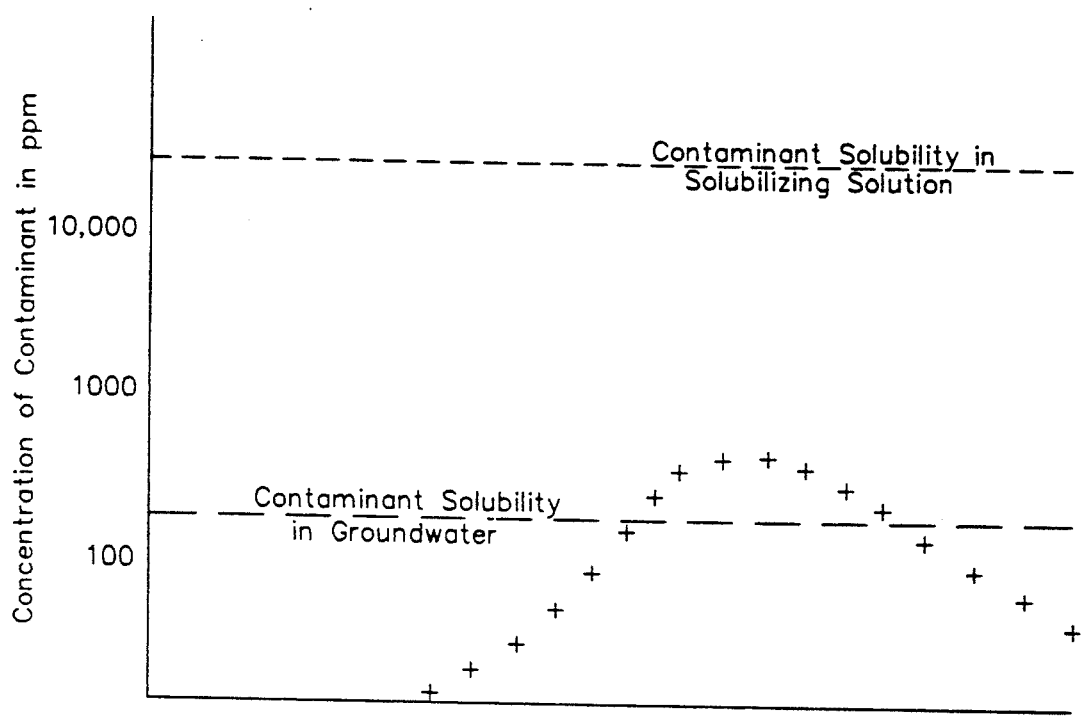
FIG. 4 is an illustration of the variation of contaminant concentration from solubilizing solution produced from a well under conditions sketched in FIG. 3.

Referring to FIG. 4, a graph of the concentration of contaminant produced from well 40 after the aqueous volume is pumped from the well is shown. Preferably, a number of samples of the produced fluid are analyzed to define the curve, as shown by the symbols on the graph. Contaminant is not present in the produced samples for a period until the aqueous solubilizing solution which had been in contact with contaminant droplets 18 or contaminant pool 20 is produced back through the well 40. At that time the concentration of contaminant in the produced fluid samples significantly increases. The concentration then decreases as the solubilizing solution is produced back from the uncontaminated zone surrounding well 40. The gradual increase in concentration of contaminant in the solution samples is largely caused by dispersion mixing of the solubilization solution with the groundwater as they flow through the permeable zone 16. The volume of samples produced before increased concentration of contaminant is produced can be used to calculate the radial distance from the well where contaminant does not exist. Volumetric calculations, using the calculated volume of fluid in the zone 16 versus radius from the well, may be used to predict the distance to segments around the well which have been contacted by the solubilizing solution samples and which contained contaminant. Alternatively, numerical codes designed to interpret the data can be used to predict the segments of the permeable zone 16 around the well 40 which have been contacted by the solubilizing solution samples. Such codes may include effects of dispersion of the solubilizing solution as it flows through zone 16.

Figure 5:
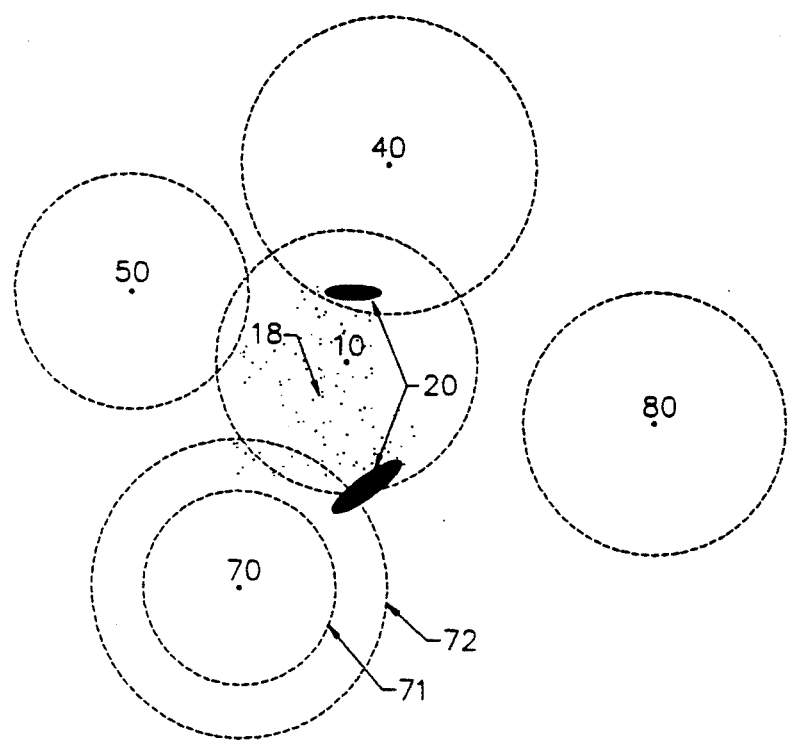
FIG. 5 is an areal view of five wells drilled in a formation containing NAPL between the wells.

FIG. 5 is an aerial view of wells 10, 40, 50, 70 and 80 drilled into an aquifer for determining the location of free liquid contaminant. Circles around each well indicate the radius $\bar{r}$ to which injected solubilizing solution has penetrated around each well. Solubilizing solutions injected in wells 50 and 80 will produce no concentrations of contaminant above the solubility in water, although water produced from these wells may contain contaminant which has dissolved from liquid at some other location in the aquifer. Likewise, solubilizing solution injected into well 70 out to the smaller radius 71 intersects no liquid contaminant and is produced back contaminant-free. However, solubilizing solution injected in a second cycle into well 70 after production back of the first solubilizing solution injected, the second cycle of solution extending out to the larger radius 72, intersects pool of contaminant 20. Solubilizing solution produced after the second cycle shows an increase in contaminant concentration of the type shown in FIG. 4. A volumetric calculation may be performed to determine the radius at which the contaminant was contacted. Contaminant produced from well 70 is chemically analyzed to determine the composition of the contaminant such that the solubilizing solution may be altered in composition to be more effective in solubilizing the contaminant and to inform engineers planning remediation of the site as to what types of contaminants will be present. A test in well 40 likewise shows contact with a contaminant at a distance removed from the well, and volumetric calculations can be performed to determine the distance from the well at which the contaminant was contacted. Testing in well 10 with solubilizing solution injection and production will show contaminant in the immediate vicinity of th well, although free liquid contaminant will not flow into the well.

Preferably a non-reactive tracer is added to the solubilizing solution. Tracers used in the solubilizing solution should have minimal effect on the solubilization process. Preferably the tracers are inorganic anions such as iodide or bromide, added in the form of common salts. Alternatively, tracers such as thiocyanate may be used, which are well known in the art. Analysis of the inorganic anions may be continuous by the use of ion-specific electrodes, which are well-known in the art. The inert tracer analysis provides a measure of the produced concentration of the injected solubilizing solution.

Solubilizing material is preferably a surfactant or mixture of surfactants. The surfactant solution is prepared at the surface in a concentration range preferably from about 0.5 to about 5.0% by weight using clean groundwater from the site. The concentration of surfactant should be in excess of the critical micelle concentration and will be determined on the basis of its ability to solubilize the contaminant expected at the site. Preferably the interfacial tension between the solubilizing solution and the contaminant will not be excessively reduced, because the purpose of the solubilizing solution is to bring samples of the contaminant back to the surface, not to displace contaminant in the subsurface formation. Minimizing the reduction in interfacial tension achieves this purpose more effectively. The surfactant chosen will preferably be non-toxic and biodegradable. The residual surfactant not produced back from the geologic formation may act as a primary carbon source for the biodegradation of residual contaminant following the test period.

Surfactants employed in the method of this invention are preferably non-ionic and anionic surfactants which are biodegradable. Among suitable surfactants are nonylphenol ethoxylates, such as WITCONOL, NP-100. This surfactant may be coupled with the phosphate esther of the same surfactant, such as EMPHOS CS-141. These chemicals are available from WITCO Corporation of Houston, Tex. Many other surfactants and mixtures of surfactants can be used which are known to be solubilizers for the contaminants present at any site. The surfactant solution should be miscible with water in all portions. Preferably, a survey is made of possible contaminants which may be present at the site and this is used in conjunction with the analysis of contaminants in the groundwater. With the initial prediction of contaminants likely to be present, surfactant solutions are formed in the laboratory and contacted with the expected contaminant. The amount of solubilized contaminant is measured at different concentrations of solubilizing solution in the groundwater. Also in the laboratory, columns are formed of soil or rock samples from the site. The surfactant solutions are flowed through such columns to determine the retardation of surfactant with respect to flow of groundwater. Retardation is caused by adsorption of the surfactant solution upon the solids of the sample. Preferably, retardation is minimized in the selected surfactant.

Analysis of surfactants for concentration is performed by techniques well-known in the industry. For example, the book by M. J. Rosen, *Surfactants and Interfacial Phenomena*, 1989, discusses various types of surfactants and some of the analytical techniques available to measure concentrations. Laboratory evaluation methods for screening potential surfactant mixtures and measuring surfactant/aquifer interactions are discussed by Fountain et al, "The Use of Surfactants for in-situ Extraction of Organic pollutants from a Contaminated Aquifer," *J. Hazardous Materials*, Vol. 28, pp. 295–311 (1991).

The analysis of contaminants produced back from the wells with the solubilizing solution is ordinarily performed by gas chromatography. The concentration of contaminants such as trichloroethylene and other common DNAPLs is readily measured using gas chromatography. LNAPLs can also be analyzed by such techniques, as is well known in the industry.

Although solubilizing solutions containing surfactants are preferred, other solutions which increase the solubility of the contaminant above its saturation concentration in groundwater are suitable. Co-solvents, such as alcohols and ketones, with water can be used in the methods of this invention. Preferably, the co-solvents should have low solubility in the contaminant. The co-solvent solution should be miscible with water in all proportions.

The composition of a NAPL around a well can be determined by injecting and producing a solubilizing solution. As long as the solution contacts the NAPL it will be solubilized and can be brought to the surface for chemical analysis. The surfactant solution should be selected to solubilize all components of the NAPL expected to be present. A mixture of the components of NAPL should be prepared in the laboratory and used to select the surfactant or mixture of surfactants. After samples of produced NAPL have been analyzed, the surfactant composition may be altered so as to improve the solubilization of the NAPL.

EXAMPLE 1

Groundwater is contaminated by chlorinated hydrocarbons (DNAPLs) believed to originate from leakage of a storage tank and from a variety of spills over a period of years. Although movement of the groundwater is at a velocity of less than 100 meters per year, a plume of contaminated groundwater exists for thousands of meters and hundreds of acres. Monitoring wells show the presence of dissolved chlorinated hydrocarbons in a permeable strata with a porosity of 30 per cent at a depth between 40 and 50 feet below the surface of the earth. No free liquid of chlorinated hydrocarbon has been produced from any of the monitoring wells drilled. Using all geologic information and information regarding movement of groundwater and possible location of the source of the contaminant, monitoring wells are concentrated in an area. The wells contain screens in the permeable zone between 40 and 50 feet and do not significantly penetrate a low permeability layer below 50 feet. Samples of groundwater from these wells contain concentrations of chlorinated hydrocarbons greater than the recommended safe levels for drinking water.

Using a mixture of chlorinated hydrocarbons approximating the mixture in the dissolved hydrocarbons, the capacity of a variety of surfactant solutions for solubilizing these chlorinated hydrocarbons is measured in the laboratory. A mixture of nonionic and anionic biodegradable surfactants is selected. Using samples of solids obtained from coring the zone between 40 and 50 feet, the retardation of various surfactant solutions is measured as the solutions flow through the solid samples. It is determined that retardation of the mixture of selected surfactants is small.

A volume of 16,000 gallons of 2% surfactant solution is mixed with the groundwater produced from one of the wells. Sodium iodide is added to the surfactant solution to produce an iodide ion tracer concentration of 1000 ppm.

In one of the monitoring wells, Well A, producing a concentration of about 80 ppm chlorinated hydrocarbons, one of the highest concentrations among the wells observed, a volume of 1000 gallons of solubilizing solution is injected. A pump is then placed in Well A and production of fluid begun. During production, the concentration of contaminant in the produced fluid is zero for a large part of the volume of injected fluid produced. The concentration of contaminant in the produced fluids eventually rises toward the initial concentration in produced fluids from this well and never exceeds that concentration. It is concluded that no free liquid contaminant exists within the effective radius of the injected solubilizing solution. It is calculated that the effective radius tested in this permeable layer is 15 feet.

In another monitoring well, Well B, spaced at a distance of 100 feet from Well A, a volume of the same solubilizing solution of 44,000 gallons was injected and produced. During the production phase, after a significant volume of zero concentration of contaminant is observed, the concentration rises rapidly to a concentration greater than the solubility of contaminant in groundwater. It is calculated that this contaminant is solubilized at a radius of about 25 feet from Well B.

An additional well, Well C, is drilled in the area where the free liquid contaminant is believed to be most likely. No free liquid can be pumped from the well. A volume of 1,000 gallons of solubilizing solution is injected and produced. On initial production of the solubilizing solution the concentration of contaminant is fifteen-times the solubility of contaminant in groundwater. This indicates that the well is very near or surrounded by free liquid contaminant at a saturation below which it will flow through the formation. An analysis of the contaminant in the solubilized solution from Well C is performed to determine the relative concentrations of various chlorinated hydrocarbons in the free liquid. Groundwater remediation techniques are employed in the area to remove the DNAPLs.

EXAMPLE 2

In Wells A and B of Example 1, the solubilizing solution is injected in Well A and Well B is pumped until the surfactant concentration in fluids produced from Well B is above the critical micelle concentration. Analysis of the fluid shows no contaminant, which leads to the conclusion that no contaminant is present along the shortest flow path between Well A and Well B. This information further limits the area of the aquifer in which remediation operations are planned. Then additional wells are used to inject and produce solubilizing solution to delineate the area of the formation which contains contaminating liquid. A geologic map is drawn encompassing the area where the liquids exist.

It is apparent that many modifications and variations of this invention as hereinabove set forth may be made without departing from the spirit and scope thereof. The specific embodiments described are given by way of example only and the invention is limited only by the terms of the appended claims.

What is claimed is:

1. A method for determining the location of non-aqueous phase liquid (NAPL) in a subsurface formation penetrated by one or more wells comprising:
   (a) providing one or more wells and injecting into a well a water-miscible solubilizing solution capable of dissolving a concentration of NAPL greater that the solubility of the NAPL present in water produced from the formation, the solubilizing solution being injected so as to flow into a location in the formation to be tested for the presence of NAPL;
   (b) producing the solubilizing solution injected in step (a) from a well as a plurality of sampling volumes;
   (c) chemically analyzing the produced solubilizing solution of step (b) to determine the concentration of NAPL in each of a plurality of sampling volumes produced; and
   (d) determining the location of NAPL in the formation from the concentrations of NAPL in the sampling volumes produced from the location in the formation tested for the presence of NAPL.

2. The method of claim 1 wherein the solubilizing solution is a solution of surfactant at a concentration above the critical micelle concentration.

3. The method of claim 2 wherein the surfactant solution is selected to solubilize all components of a NAPL expected to be present in the formation.

4. The method of claim 1 wherein an inert tracer is added to the solubilizing solution before injection of step (a) and analyzed in the produced solution to determine produced concentrations of the injected solubilizing solution.

5. The method of claim 1 wherein the solubilizing solution is injected in step (a) and produced in step (b) from the same well.

6. The method of claim 5 wherein a wellbore segment of the well is selected and flow is isolated to the selected wellbore segment.

7. The method of claim 5 wherein volumes of solubilizing solution are injected and produced through two or more cycles.

8. The method of claim 7 wherein the volumes of solubilizing solution are increased each cycle.

9. The method of claim 1 further comprising the step of determining the location of the injected solution in the formation after step (a).

10. The method of claim 1 further comprising the step of repeating steps (a)-(d) in a plurality of wells providing flow into or out of a geologic formation to locate an area of the formation containing NAPL.

11. The method of claim 1 wherein the composition of the solubilizing solution is altered after samples of produced NAPL have been analyzed.

12. A method for determining the composition of non-aqueous phase liquid (NAPL) in a subsurface formation penetrated by one or more wells comprising:
   (a) providing one or more wells drilled into a subsurface formation containing NAPL and injecting into a well an amount of water-miscible solubilizing solution sufficient to contact the liquid;

(b) producing the solubilizing solution injected in step (a) from a well; and (c) chemically analyzing the produced solubilizing solution of step (b) thereby determining the fraction of each chemical component of NAPL present.

13. The method of claim 12, wherein the solubilizing solution is a solution of surfactant.

14. The method of claim 13 wherein the solubilizing solution is selected to solubilize all components of a NAPL expected to be present in the formation.

15. The method of claim 12 wherein the solubilizing solution is injected in step (a) and produced in step (b) from the same well.

16. The method of claim 15 wherein different compositions of solubilizing solution are injected and produced through two or more cycles.

* * * * *